(12) United States Patent
Zou et al.

(10) Patent No.: US 9,950,024 B2
(45) Date of Patent: Apr. 24, 2018

(54) TRADITIONAL CHINESE MEDICINE COMPOSITION AND THE USE THEREOF

(71) Applicant: INFINITUS (CHINA) COMPANY LTD., Jiang Men, Guangdong (CN)

(72) Inventors: Shiyu Zou, Jiang Men (CN); Jiangping Li, Jiang Men (CN); Chung Wah Ma, Jiang Men (CN)

(73) Assignee: INFINITUS (CHINA) COMPANY LTD., Jiang Men, Guangdong (CN)

( * ) Notice: Subject to any disclaimer, the term of this patent is extended or adjusted under 35 U.S.C. 154(b) by 188 days.

(21) Appl. No.: 15/164,844

(22) Filed: May 25, 2016

(65) Prior Publication Data

US 2016/0375083 A1 Dec. 29, 2016

(30) Foreign Application Priority Data

Jun. 29, 2015 (CN) .......................... 2015 1 0372959

(51) Int. Cl.

| A61K 36/00 | (2006.01) |
|---|---|
| A61K 36/899 | (2006.01) |
| A61K 36/355 | (2006.01) |
| A61K 36/752 | (2006.01) |
| A61K 35/644 | (2015.01) |
| A61K 36/734 | (2006.01) |
| A61K 36/87 | (2006.01) |
| A61K 9/00 | (2006.01) |
| A23L 2/52 | (2006.01) |
| A23L 2/02 | (2006.01) |
| A61K 36/8998 | (2006.01) |
| A61K 47/26 | (2006.01) |

(52) U.S. Cl.
CPC .............. *A61K 36/899* (2013.01); *A23L 2/02* (2013.01); *A23L 2/52* (2013.01); *A61K 9/0095* (2013.01); *A61K 35/644* (2013.01); *A61K 36/355* (2013.01); *A61K 36/734* (2013.01); *A61K 36/752* (2013.01); *A61K 36/87* (2013.01); *A61K 36/8998* (2013.01); *A61K 47/26* (2013.01); *A23V 2002/00* (2013.01)

(58) Field of Classification Search
CPC ..................................................... A61K 36/00
USPC ......................................................... 424/725
See application file for complete search history.

(56) References Cited

FOREIGN PATENT DOCUMENTS

| CN | 102511880 A | 6/2012 |
|---|---|---|
| CN | 102940812 A * | 2/2013 |
| CN | 103417876 A | 12/2013 |

* cited by examiner

*Primary Examiner* — Michael V Meller
(74) *Attorney, Agent, or Firm* — U.S. Fairsky LLP; Yue Xu

(57) ABSTRACT

The present invention relates to the technical field of Traditional Chinese medicine, in particular to a traditional Chinese medicine composition and the use thereof. The traditional Chinese medicine composition comprises the following ingredients: honeysuckle, tangerine peel, stir-baked malt, honey, and hawthorn juice. The traditional Chinese medicine composition of the present invention has significant promotions on the gastric emptying rate, intestinal motility, gastric digestive enzyme (pepsin) activity and pancreatic enzyme (trypsin, chymotrypsin, amylase and lipase) activity of rats, exhibiting that the traditional Chinese medicine composition of the present invention has significant effects of clearing heat-fire and moistening the intestine.

2 Claims, No Drawings

TRADITIONAL CHINESE MEDICINE COMPOSITION AND THE USE THEREOF

FIELD OF THE INVENTION

The present invention relates to the technical field of traditional Chinese medicine, in particular to a traditional Chinese medicine composition and the use thereof.

BACKGROUND OF THE INVENTION

The highly competitive modern society results in the rise of depletion fire syndrome going up in the body for many people due to overwork, mental stress, uncontrolled diet, poor sleep and other reasons, inducing various symptoms from dryness and heat such as rough skin, acne, bad breath, toothache, oral ulcers, constipation and the like. These symptoms from dryness and heat can be adjusted by daily diet. While there is an increasing demand for natural and healthy juice beverage or other healthy food with the improvement of people's living standards and health consciousness, currently most of the juice beverage on the market is formulated by the addition of various flavors, fragrances, artificial sweeteners and pigments with low juice content and inappropriate formulation design, where the artificial sweeteners and pigments added even become disadvantages to the health, and the inappropriate formulation design lacks the factors regarding health concept, with little regulation to the symptoms from dryness and heat in everyday life; as most of the health food on the market has little effect on the treatment of the symptoms from dryness and heat, the provision of juice beverage or other types of health food that clear heat-fire and moisten the intestine may fill the gap in the market.

The patent document with a patent publication number of CN 102511880 A discloses a thick pulp comprising honeysuckle, chrysanthemum, cassia seed and hawthorn, where this novel nutritive beverage has full nutritive components with the convenience of consumption and easiness of uptake, to help in invigorating spleen-stomach and replenishing Qi, clearing heat, removing toxins, strengthening the spleen and stomach, nourishing the blood, strengthening the mind, nourishing the liver and kidney, benefiting the marrow, improving eyesight, improving body immunity and other effects, and is a suitable nutritive food for four seasons. However, in practical application, the nutritive beverage has suboptimal effects of clearing heat-fire and moistening the intestine.

The patent document with a patent publication number of CN 103417876 A discloses a digestion-detoxification tablet, the main components of which include hawthorn, Chinese yam, massa medicata fermentata, tangerine peel, malt, *Coptis chinensis*, honeysuckle, isatis, rhubarb, ginseng, licorice, bears bile powder, musk powder, borneol powder, notoginseng powder, salvia powder and the like, but the digestion-detoxification tablet not only contains expensive traditional Chinese medicines, but also has a less-than-ideal effect of clearing heat-fire and moistening the intestine in practical applications, failing to meet the needs of modern people.

For the reasons above, the development of health food that clears heat-fire and moistens the intestine to meet the needs of modern people has important practical significance.

SUMMARY OF THE INVENTION

In view of this, the present invention provides a traditional Chinese medicine composition and the use thereof. The traditional Chinese medicine composition has significant promotions on the gastric emptying rate, intestinal motility, gastric digestive enzyme (pepsin) activity and pancreatic enzyme (trypsin, chymotrypsin, amylase and lipase) activity of rats, exhibiting that the traditional Chinese medicine composition of the present invention has significant effects of clearing heat-fire, moistening the intestine.

To achieve the above object of the invention, the present invention provides the following technical solutions:

The present invention provides a traditional Chinese medicine composition comprising the following ingredients: honeysuckle, tangerine peel, stir-baked malt, honey, and hawthorn juice.

Hawthorn is a unique species in China, and may be divided into "north hawthorn" and "south hawthorn" according to where it is cultivated with a larger cultivation amount of north hawthorn. Hawthorn fruit has abundant nutrition, in which the content of calcium and magnesium are the highest among various fruits. Its high content of vitamin C is only behind that of fresh jujube and kiwi, and is three times higher than orange. It also contains nutrients such as protein, amino acids, carbohydrates, crude fiber, carotene and the like. The medicinal value of hawthorn that has been recorded in "Shen Nong's Herbal Classic" lies in the functions of promoting fluid production, quenching thirst, elimination stagnant food, helping digestion, promoting blood circulation, removing blood stasis and the like. Modern medical research shows that: the organic acids and flavonoids in hawthorn have preventive and therapeutic effects on the diseases in digestive and cardiovascular system.

Honeysuckle: According to the records in "Chinese Pharmacopoeia", honeysuckle has significant heat-clearing and detoxicating effects and is used widely in the civil society as a medicinal and edible Chinese herbal medicine for a long time. Honeysuckle has always been known as a heat-clearing and detoxicating medicine. It clears heat without hurting the stomach due to its sweet and cool property, and penetrates to eliminate pathogens due to its aroma. Honeysuckle is able to dispel wind-heat and eliminate blood toxins, and has significant effects when used in the treatment of various diseases from heat, such as fever, rash, spots, carbuncle from heat toxins, sore throat and the like.

Tangerine peel: According to the records in "Chinese Pharmacopoeia 2010", Tangerine peel that is bitter, pungent and warm goes to the spleen and lung channels and has the effects of regulating Qi, strengthening the spleen, eliminating dampness and dissipating phlegm, in which the main effect is the activation of the spleen and stomach Qi. The spleen and stomach act mainly to transport moisture, so the smooth operation of the spleen and stomach Qi will result in the elimination of dampness, invigoration of the spleen and the dissipation of phlegm, and in other words, the spleen is nourished by the warmness of the tangerine peel, refreshed by the pungency and strengthened by the bitterness. Since the tangerine peel mainly activate the spleen and stomach Qi, and the spleen and stomach are located in middle energizer, the activation of Qi in middle energizer allows the Qi in triple energizer to flow with it. The triple energizer as the organ in charge of water circulation circulates the aqueous liquid while accompanying moisture; and as a peripheral organ of the viscera reaches up to the heart and lung and down to the liver and kidney. Consequently, the tangerine peel may have effects in a wide range of all the viscera throughout the whole body in dampness. As pointed out by Li Shizhen, "the tangerine peel with the bitterness to purge and dry and the pungency to dispel and reconcile may cure all diseases based on its effects of regulating Qi and eliminating dampness.

Malt: According to the records in "Chinese Pharmacopoeia": malt that is sweet and flat goes to the spleen and stomach channels and may activate Qi, help digestion, strengthen the spleen and act as an appetizer. Use of malt as a medicine first appeared in "Mingyi Bielu" by Tao Jinghong in Liang Dynasty. "Yixue Qiyuan" records: malt can "replenish the deficiency in the spleen and stomach, and ease the stomach and intestine"; "Bengcao Jingshu" records: "malt has the same function as rice bud with a stronger effect to help digestion, and the Qi it generates can aid in the rise of the stomach-Qi, activate the Yang channels and assist with the healthy circulation, so it acts mainly as an appetizer to benefit the spleen and help digest water, grain and all other stagnant, cold and bulging food. "Compendium of Materia Medica" records: malt can "help digest all the stagnant rice, wheat and fruits".

Honey: "Chinese Pharmacopoeia" records: Honey is sweet and flat. It goes into the lung, spleen and colon channels. It has the effects of invigorating the middle energizer, moistening dryness, relieving pain and detoxicating, as well as promoting granulation and astringing sores when used externally. It may be used in the treatment of abdominal pain, lung dryness and cough, intestine dryness and constipation, and intoxication by aconitum; it may also be used in the treatment of sore and ulcer that are not astringed, and scald by water and fire when used externally.

In the present invention, a traditional Chinese medicine composition is prepared without the addition of flavors, fragrances, artificial sweeteners and pigments, using hawthorn juice, honeysuckle, tangerine peel, stir-baked malt and honey as the main ingredients based on the traditional Chinese medicine theory by adding choice medicinal and edible traditional Chinese medicine and natural and healthy food ingredients through scientific formulation design, and the obtained traditional Chinese medicine compositions of the present invention with a high content of juice have the effects of clearing heat-fire, moistening the intestine.

Preferably, the following components are included based on parts by weight,

| Honeysuckle | 0.5 to 10 parts |
| Tangerine peel | 0.5 to 10 parts |
| Stir-baked malt | 0.5 to 10 parts |
| Honey | 5 to 20 parts |
| Hawthorn juice | 5 to 20 parts. |

The present invention also provides a method for preparing the traditional Chinese medicine composition comprising the steps of:

The honeysuckle, tangerine peel and stir-baked malt are mixed and extracted with water to obtain an extract;

The honey, hawthorn juice and the extract are mixed to obtain the traditional Chinese medicine composition.

Preferably, the traditional Chinese medicine composition further comprises crystal sugar.

Crystal sugar: crystal sugar that is sweet and flat goes into the lung and spleen channels; it has the effects of nourishing the middle energizer, benefiting Qi, regulating the stomach and moistening the lung; and crystal sugar nourishes Yin, promotes fluid production, moistens the lung and relieves cough, and has excellent effects of helping in the treatment of lung dryness and cough, dry cough without sputum and cough with bloody sputum. In the civil society, people of all ages use crystal sugar when cooking a variety of nourishing food.

Preferably, the following components are included based on parts by weight,

| Honeysuckle | 0.5 to 10 parts |
| Tangerine peel | 0.5 to 10 parts |
| Stir-baked malt | 0.5 to 10 parts |
| Honey | 5 to 20 parts |
| Hawthorn juice | 5 to 20 parts |
| Crystal sugar | 5 to 20 parts. |

The present invention also provides a method for preparing the traditional Chinese medicine composition comprising the steps of:

The honeysuckle, tangerine peel and stir-baked malt are mixed and extracted with water to obtain an extract;

The crystal sugar, honey, hawthorn juice and the extract are mixed to obtain the traditional Chinese medicine composition.

Preferably, the traditional Chinese medicine composition further comprises sugar cane juice.

Sugarcane: Sugarcane as a good dietetic food is sweet, cool, and capable of clearing, moistening, and nourishing, and the juicy and sweet sugar cane with abundant nutrition known as an excellent fruit among others was included in "tonic" by ancient Chinese medical scientists. According to the records in "Chinese Materia Medica", sugar cane that is sweet and cold goes to the lung and stomach channels, and has the effects of clearing heat, detoxicating, promoting liquid production, relieving thirst, regulating the stomach, preventing vomit, nourishing Yin and moistening dryness, as well as an excellent alleviative effects for symptoms such as parched mouth and dry tongue, liquid deficiency, difficult urination, dry stools, indigestion, nausea and vomit, hiccups, high fever and thirst and the like.

Preferably, the following components are included based on parts by weight,

| Honeysuckle | 0.5 to 10 parts |
| Tangerine peel | 0.5 to 10 parts |
| Stir-baked malt | 0.5 to 10 parts |
| Honey | 5 to 20 parts |
| Hawthorn juice | 5 to 20 parts |
| Crystal sugar | 5 to 20 parts |
| Sugar cane juice | 10 to 30 parts. |

The present invention also provides a method for preparing the traditional Chinese medicine composition comprising the steps of:

The honeysuckle, tangerine peel and stir-baked malt are mixed and extracted with water to obtain an extract;

The crystal sugar, honey, hawthorn juice, sugar cane juice and the extract are mixed to obtain the traditional Chinese medicine composition.

Preferably, the following components are included based on parts by weight,

| Honeysuckle | 0.5 to 10 parts |
| Tangerine peel | 0.5 to 10 parts |
| Stir-baked malt | 0.5 to 10 parts |
| Honey | 5 to 20 parts |
| Hawthorn juice | 5 to 20 parts |
| Sugar cane juice | 10 to 30 parts |

The present invention also provides a method for preparing the traditional Chinese medicine composition comprising the steps of:

The honeysuckle, tangerine peel and stir-baked malt are mixed and extracted with water to obtain an extract;

The honey, hawthorn juice, sugar cane juice and the extract are mixed to obtain the traditional Chinese medicine composition.

Preferably, the traditional Chinese medicine composition further comprises grape juice.

Grape, the fruit of grape in vitaceae, functions to: tonifying Qi and blood, strengthen bones, benefit urination; and treat the symptoms such as weakness of Qi and blood, deficiency in lung-Qi and cough, palpitation and night sweats, rheumatism and arthralgia, gonorrhea and edema.

Preferably, the following components are included based on parts by weight,

| | |
|---|---|
| Honeysuckle | 0.5 to 10 parts |
| Tangerine peel | 0.5 to 10 parts |
| Stir-baked malt | 0.5 to 10 parts |
| Crystal sugar | 5 to 20 parts |
| Honey | 5 to 20 parts |
| Hawthorn juice | 5 to 20 parts |
| Sugar cane juice | 10 to 30 parts |
| grape juice | 2 to 10 parts. |

The present invention also provides a method for preparing the traditional Chinese medicine composition comprising the steps of:

The honeysuckle, tangerine peel and stir-baked malt are mixed and extracted with water to obtain an extract;

The crystal sugar, honey, hawthorn juice, sugar cane juice, grape juice and the extract are mixed to obtain the traditional Chinese medicine composition.

In the present invention, a traditional Chinese medicine composition is prepared without the addition of flavors, fragrances, artificial sweeteners and pigments, using hawthorn juice, sugar cane juice, grape juice, honeysuckle, tangerine peel, stir-baked malt, crystal sugar and honey as the main ingredients based on the traditional Chinese medicine theory by adding choice medicinal and edible traditional Chinese medicine and natural and healthy food ingredients through scientific formulation design, and the obtained traditional Chinese medicine compositions of the present invention with a high content of juice have the effects of clearing heat, lowering fire and moistening intestine.

Preferably, the following components are included based on parts by weight,

| | |
|---|---|
| Honeysuckle | 0.5 to 10 parts |
| Tangerine peel | 0.5 to 10 parts |
| Stir-baked malt | 0.5 to 10 parts |
| Honey | 5 to 20 parts |
| Hawthorn juice | 5 to 20 parts |
| Sugar cane juice | 10 to 30 parts |
| grape juice | 2 to 10 parts. |

The present invention also provides a method for preparing the traditional Chinese medicine composition comprising the steps of:

The honeysuckle, tangerine peel and stir-baked malt are mixed and extracted with water to obtain an extract;

The honey, hawthorn juice, sugar cane juice, grape juice and the extract are mixed to obtain the traditional Chinese medicine composition.

Preferably, the following components are included based on parts by weight,

| | |
|---|---|
| Honeysuckle | 0.5 to 10 parts |
| Tangerine peel | 0.5 to 10 parts |
| Stir-baked malt | 0.5 to 10 parts |
| Crystal sugar | 5 to 20 parts |
| Honey | 5 to 20 parts |
| Hawthorn juice | 5 to 20 parts |
| grape juice | 2 to 10 parts. |

The present invention also provides a method for preparing the traditional Chinese medicine composition comprising the steps of:

The honeysuckle, tangerine peel and stir-baked malt are mixed and extracted with water to obtain an extract;

The crystal sugar, honey, hawthorn juice, grape juice and the extract are mixed to obtain the traditional Chinese medicine composition.

Preferably, the following components are included based on parts by weight,

| | |
|---|---|
| Honeysuckle | 0.5 to 10 parts |
| Tangerine peel | 0.5 to 10 parts |
| Stir-baked malt | 0.5 to 10 parts |
| Honey | 5 to 20 parts |
| Hawthorn juice | 5 to 20 parts |
| grape juice | 2 to 10 parts |

The present invention also provides a method for preparing the traditional Chinese medicine composition comprising the steps of:

The honeysuckle, tangerine peel and stir-baked malt are mixed and extracted with water to obtain an extract;

The honey, hawthorn juice, grape juice and the extract are mixed to obtain the traditional Chinese medicine composition.

In some embodiments provided in the present invention, there are 0.5 parts of honeysuckle, 1 part of tangerine peel, 5 parts of stir-baked malt, 5 parts of crystal sugar, 10 parts of honey, 15 parts of hawthorn juice, 30 parts of sugar cane juice and 2 parts of grape juice based on parts by weight.

In further embodiments provided in the present invention, there are 1 part of honeysuckle, 5 parts of tangerine peel, 10 parts of stir-baked malt, 10 parts of crystal sugar, 15 parts of honey, 20 parts of hawthorn juice, 10 parts of sugar cane juice and 5 parts of grape juice based on parts by weight.

In further embodiments provided in the present invention, there are 5 parts of honeysuckle, 10 parts of tangerine peel, 0.5 parts of stir-baked malt, 15 parts of crystal sugar, 20 parts of honey, 5 parts of hawthorn juice, 20 parts of sugar cane juice and 8 parts of grape juice based on parts by weight.

In further embodiments provided in the present invention, there are 10 parts of honeysuckle, 0.5 parts of tangerine peel, 1 part of stir-baked malt, 20 parts of crystal sugar, 5 parts of honey, 10 parts of hawthorn juice, 25 parts of sugar cane juice and 10 parts of grape juice based on parts by weight.

The present invention also provides a method for preparing the traditional Chinese medicine composition comprising the steps of:

The honeysuckle, tangerine peel and stir-baked malt are mixed and extracted with water to obtain an extract;

The crystal sugar, honey, hawthorn juice, sugar cane juice, grape juice and the extract are mixed to obtain the traditional Chinese medicine composition.

In some embodiments provided in the present invention, the extraction with water specifically includes: addition of 10 to 15 times of water, extraction at 90 to 100° C. for 2 to 3 hours, and repeated extractions for 2 or 3 times.

The present invention also provides use of the traditional Chinese medicine composition in the preparation of drugs or health food having the effects of clearing heat, lowering fire and moistening the intestine.

The present invention also provides a juice beverage comprising the traditional Chinese medicine composition provided in the present invention.

The present invention provides a traditional Chinese medicine composition, preparation methods and uses thereof. The traditional Chinese medicine composition comprises the following ingredients: honeysuckle, tangerine peel, stir-baked malt, honey, and hawthorn juice. The present invention has at least one of the following advantages:

The experimental results with respect to its effects indicate: The obtained composition of the present invention may significantly improve the gastric emptying rates (24% to 30%) of rats, which are substantially higher than those of Control A (8%) and Control B (17%); the obtained composition of the present invention may significantly improve the intestinal motility of rats (24% to 28%), which are substantially higher than those of Control A (5%) and Control B (15%); the obtained composition of the present invention may significantly improve the pepsin activity (26% to 32%) of rats, which are substantially higher than those of Control A (10%) and Control B (16%); the obtained composition of the present invention may significantly improve the trypsin (10% to 14%), chymotrypsin (14% to 16%), amylase (22% to 27%) and lipase (40% to 44%) activity of rats, which are substantially higher than those of Control A and Control B. As can be seen, the obtained composition of the present invention has significant promotions on the gastric emptying rate, intestinal motility, gastric digestive enzyme (pepsin) activity and pancreatic enzyme (trypsin, chymotrypsin, amylase and lipase) activity of rats, which are superior to those of Control A and Control B, exhibiting that the traditional Chinese medicine composition of the present invention has significant effects of clearing heat, lowering fire and moistening the intestine.

Choice traditional Chinese medicines and food ingredients, that is, honeysuckle, tangerine peel, stir-baked malt, hawthorn juice, honey, sugar cane juice, grape juice and crystal sugar are employed in the present invention without the addition of flavors and fragrances, artificial sweeteners and pigments, resulting in a high juice content, abundant nutrition and unique taste.

DETAILED DESCRIPTION

The present invention discloses a traditional Chinese medicine composition and the use thereof, which may be implemented with suitable modifications of the process parameters by those skilled in the art in light of the present disclosure. It is of particular note that all the similar alterations and modifications are clear to those skilled in the art and deemed to be included in the present invention. Methods and uses of the present invention have been described by the preferred examples, and it is obvious that those in related art are able to make changes or appropriate alternations and the combinations thereof to the methods and uses described herein to implement and apply the inventive technology without departing from the disclosure, spirit and scope of the present invention.

The ingredients or auxiliaries used in the traditional Chinese medicine composition and the use thereof in the present invention are all commercially available. Among them, the hawthorn juice, sugar cane juice and grape juice are concentrated fruit juice, wherein hawthorn juice has a soluble solids content of 59%, sugar cane juice has a soluble solids content of 58%, and grape juice has a soluble solids content of 65%.

The present invention is further explained in combination with the examples below.

Example 1 The Preparation of the Traditional Chinese Medicine Composition

Extraction: 0.5 g honeysuckle, 1 g tangerine peel and 5 g stir-baked malt were weighed in proportion according to the formulation, and these materials were put into an extraction tank, then after the addition of 10 times of water the extraction was performed at 92° C. for 3 hours and repeated twice to obtain an extract, which was concentrated into a concentrate with a soluble solids content of 15-25%.

Formulation: the ingredients were weighed in proportion according to the formulation, and to the formulation tank were added: 31.5 g water, 5 g crystal sugar, 10 g honey, 15 g hawthorn juice, 30 g sugar cane juice, 2 g grape juice and the concentrate described above. After the intermediates were stirred continuously for 10-15 min, the stirring was stopped and a sample was removed for tests, and after passing the tests, the traditional Chinese medicine composition was obtained.

Example 2 The Preparation of the Traditional Chinese Medicine Composition

Extraction: 1 g honeysuckle, 5 g tangerine peel and 10 g stir-baked malt were weighed in proportion according to the formulation, and these materials were put into an extraction tank, then after the addition of 12 times of water the extraction was performed at 95° C. for 2 hours and repeated twice to obtain an extract, which was concentrated into a concentrate with a soluble solids content of 15-25%.

Formulation: the ingredients were weighed in proportion according to the formulation, and to the formulation tank were added: 24.0 g water, 10 g crystal sugar, 15 g honey, 20 g hawthorn juice, 10 g sugar cane juice, 5 g grape juice and the concentrate described above. After the intermediates were stirred continuously for 10-15 min, the stirring was stopped and a sample was removed for tests, and after passing the tests, the traditional Chinese medicine composition was obtained.

Example 3 The Preparation of the Traditional Chinese Medicine Composition

Extraction: 5 g honeysuckle, 10 g tangerine peel and 0.5 g stir-baked malt were weighed in proportion according to the formulation, and these materials were put into an extraction tank, then after the addition of 14 times of water the extraction was performed at 100° C. for 3 hours and repeated three times to obtain an extract, which was concentrated into a concentrate with a soluble solids content of 15-25%.

Formulation: the ingredients were weighed in proportion according to the formulation, and to the formulation tank were added: 16.5 g water, 15 g crystal sugar, 20 g honey, 5 g hawthorn juice, 20 g sugar cane juice, 8 g grape juice and the concentrate described above. After the intermediates were stirred continuously for 10-15 min, the stirring was stopped and a sample was removed for tests, and after passing the tests, the traditional Chinese medicine composition was obtained.

Example 4 The Preparation of the Traditional Chinese Medicine Composition

Extraction: 10 g honeysuckle, 0.5 g tangerine peel and 1 g stir-baked malt were weighed in proportion according to the formulation, and these materials were put into an extraction tank, then after the addition of 15 times of water the extraction was performed at 90° C. for 2 hours and repeated three times to obtain an extract, which was concentrated into a concentrate with a soluble solids content of 15-25%.

Formulation: the ingredients were weighed in proportion according to the formulation, and to the formulation tank were added: 18.5 g water, 20 g crystal sugar, 5 g honey, 10 g hawthorn juice, 25 g sugar cane juice, 10 g grape juice and the concentrate described above. After the intermediates were stirred continuously for 10-15 min, the stirring was stopped and a sample was removed for tests, and after passing the tests, the traditional Chinese medicine composition was obtained.

Example 5 The Preparation of the Traditional Chinese Medicine Composition

Extraction: 0.5 g honeysuckle, 1 g tangerine peel and 5 g stir-baked malt were weighed in proportion according to the formulation, and these materials were put into an extraction tank, then after the addition of 10 times of water the extraction was performed at 92° C. for 3 hours and repeated twice to obtain an extract, which was concentrated into a concentrate with a soluble solids content of 15-25%.

Formulation: the ingredients were weighed in proportion according to the formulation, and to the formulation tank were added: 31.5 g water, 10 g honey, 15 g hawthorn juice, and the concentrate described above. After the intermediates were stirred continuously for 10-15 min, the stirring was stopped and a sample was removed for tests, and after passing the tests, the traditional Chinese medicine composition was obtained.

Example 6 The Preparation of the Traditional Chinese Medicine Composition

Extraction: 1 g honeysuckle, 5 g tangerine peel and 10 g stir-baked malt were weighed in proportion according to the formulation, and these materials were put into an extraction tank, then after the addition of 12 times of water the extraction was performed at 95° C. for 2 hours and repeated twice to obtain an extract, which was concentrated into a concentrate with a soluble solids content of 15-25%.

Formulation: the ingredients were weighed in proportion according to the formulation, and to the formulation tank were added: 24.0 g water, 15 g honey, 20 g hawthorn juice and the concentrate described above. After the intermediates were stirred continuously for 10-15 min, the stirring was stopped and a sample was removed for tests, and after passing the tests, the traditional Chinese medicine composition was obtained.

Example 7 The Preparation of the Traditional Chinese Medicine Composition

Extraction: 5 g honeysuckle, 10 g tangerine peel and 0.5 g stir-baked malt were weighed in proportion according to the formulation, and these materials were put into an extraction tank, then after the addition of 14 times of water the extraction was performed at 100° C. for 3 hours and repeated three times to obtain an extract, which was concentrated into a concentrate with a soluble solids content of 15-25%.

Formulation: the ingredients were weighed in proportion according to the formulation, and to the formulation tank were added: 16.5 g water, 20 g honey, 5 g hawthorn juice and the concentrate described above. After the intermediates were stirred continuously for 10-15 min, the stirring was stopped and a sample was removed for tests, and after passing the tests, the traditional Chinese medicine composition was obtained.

Example 8 The Preparation of the Traditional Chinese Medicine Composition

Extraction: 10 g honeysuckle, 0.5 g tangerine peel and 1 g stir-baked malt were weighed in proportion according to the formulation, and these materials were put into an extraction tank, then after the addition of 15 times of water the extraction was performed at 90° C. for 2 hours and repeated three times to obtain an extract, which was concentrated into a concentrate with a soluble solids content of 15-25%.

Formulation: the ingredients were weighed in proportion according to the formulation, and to the formulation tank were added: 18.5 g water, 5 g honey, 10 g hawthorn juice and the concentrate described above. After the intermediates were stirred continuously for 10-15 min, the stirring was stopped and a sample was removed for tests, and after passing the tests, the traditional Chinese medicine composition was obtained.

Example 9 The Preparation of the Traditional Chinese Medicine Composition

Extraction: 0.5 g honeysuckle, 1 g tangerine peel and 5 g stir-baked malt were weighed in proportion according to the formulation, and these materials were put into an extraction tank, then after the addition of 10 times of water the extraction was performed at 92° C. for 3 hours and repeated twice to obtain an extract, which was concentrated into a concentrate with a soluble solids content of 15-25%.

Formulation: the ingredients were weighed in proportion according to the formulation, and to the formulation tank were added: 31.5 g water, 5 g crystal sugar, 10 g honey, 15 g hawthorn juice and the concentrate described above. After the intermediates were stirred continuously for 10-15 min, the stirring was stopped and a sample was removed for tests, and after passing the tests, the traditional Chinese medicine composition was obtained.

Example 10 The Preparation of the Traditional Chinese Medicine Composition

Extraction: 1 g honeysuckle, 5 g tangerine peel and 10 g stir-baked malt were weighed in proportion according to the formulation, and these materials were put into an extraction tank, then after the addition of 12 times of water the extraction was performed at 95° C. for 2 hours and repeated twice to obtain an extract, which was concentrated into a concentrate with a soluble solids content of 15-25%.

Formulation: the ingredients were weighed in proportion according to the formulation, and to the formulation tank were added: 24.0 g water, 10 g crystal sugar, 15 g honey, 20 g hawthorn juice, and the concentrate described above. After the intermediates were stirred continuously for 10-15 min, the stirring was stopped and a sample was removed for tests, and after passing the tests, the traditional Chinese medicine composition was obtained.

Example 11 The Preparation of the Traditional Chinese Medicine Composition

Extraction: 5 g honeysuckle, 10 g tangerine peel and 0.5 g stir-baked malt were weighed in proportion according to the formulation, and these materials were put into an extraction tank, then after the addition of 14 times of water the extraction was performed at 100° C. for 3 hours and repeated three times to obtain an extract, which was concentrated into a concentrate with a soluble solids content of 15-25%.

Formulation: the ingredients were weighed in proportion according to the formulation, and to the formulation tank were added: 16.5 g water, 15 g crystal sugar, 20 g honey, 5 g hawthorn juice, and the concentrate described above. After the intermediates were stirred continuously for 10-15 min, the stirring was stopped and a sample was removed for tests, and after passing the tests, the traditional Chinese medicine composition was obtained.

Example 12 The Preparation of the Traditional Chinese Medicine Composition

Extraction: 10 g honeysuckle, 0.5 g tangerine peel and 1 g stir-baked malt were weighed in proportion according to the formulation, and these materials were put into an extraction tank, then after the addition of 15 times of water the extraction was performed at 90° C. for 2 hours and repeated three times to obtain an extract, which was concentrated into a concentrate with a soluble solids content of 15-25%.

Formulation: the ingredients were weighed in proportion according to the formulation, and to the formulation tank were added: 18.5 g water, 20 g crystal sugar, 5 g honey, 10 g hawthorn juice, and the concentrate described above. After the intermediates were stirred continuously for 10-15 min, the stirring was stopped and a sample was removed for tests, and after passing the tests, the traditional Chinese medicine composition was obtained.

Example 13 The Preparation of the Traditional Chinese Medicine Composition

Extraction: 0.5 g honeysuckle, 1 g tangerine peel and 5 g stir-baked malt were weighed in proportion according to the formulation, and these materials were put into an extraction tank, then after the addition of 10 times of water the extraction was performed at 92° C. for 3 hours and repeated twice to obtain an extract, which was concentrated into a concentrate with a soluble solids content of 15-25%.

Formulation: the ingredients were weighed in proportion according to the formulation, and to the formulation tank were added: 31.5 g water, 5 g crystal sugar, 10 g honey, 15 g hawthorn juice, 30 g sugar cane juice and the concentrate described above. After the intermediates were stirred continuously for 10-15 min, the stirring was stopped and a sample was removed for tests, and after passing the tests, the traditional Chinese medicine composition was obtained.

Example 14 The Preparation of the Traditional Chinese Medicine Composition

Extraction: 1 g honeysuckle, 5 g tangerine peel and 10 g stir-baked malt were weighed in proportion according to the formulation, and these materials were put into an extraction tank, then after the addition of 12 times of water the extraction was performed at 95° C. for 2 hours and repeated twice to obtain an extract, which was concentrated into a concentrate with a soluble solids content of 15-25%.

Formulation: the ingredients were weighed in proportion according to the formulation, and to the formulation tank were added: 24.0 g water, 10 g crystal sugar, 15 g honey, 20 g hawthorn juice, 10 g sugar cane juice and the concentrate described above. After the intermediates were stirred continuously for 10-15 min, the stirring was stopped and a sample was removed for tests, and after passing the tests, the traditional Chinese medicine composition was obtained.

Example 15 The Preparation of the Traditional Chinese Medicine Composition

Extraction: 5 g honeysuckle, 10 g tangerine peel and 0.5 g stir-baked malt were weighed in proportion according to the formulation, and these materials were put into an extraction tank, then after the addition of 14 times of water the extraction was performed at 100° C. for 3 hours and repeated three times to obtain an extract, which was concentrated into a concentrate with a soluble solids content of 15-25%.

Formulation: the ingredients were weighed in proportion according to the formulation, and to the formulation tank were added: 16.5 g water, 15 g crystal sugar, 20 g honey, 5 g hawthorn juice, 20 g sugar cane juice and the concentrate described above. After the intermediates were stirred continuously for 10-15 min, the stirring was stopped and a sample was removed for tests, and after passing the tests, the traditional Chinese medicine composition was obtained.

Example 16 The Preparation of the Traditional Chinese Medicine Composition

Extraction: 10 g honeysuckle, 0.5 g tangerine peel and 1 g stir-baked malt were weighed in proportion according to the formulation, and these materials were put into an extraction tank, then after the addition of 15 times of water the extraction was performed at 90° C. for 2 hours and repeated three times to obtain an extract, which was concentrated into a concentrate with a soluble solids content of 15-25%.

Formulation: the ingredients were weighed in proportion according to the formulation, and to the formulation tank were added: 18.5 g water, 20 g crystal sugar, 5 g honey, 10 g hawthorn juice, 25 g sugar cane juice and the concentrate described above. After the intermediates were stirred continuously for 10-15 min, the stirring was stopped and a sample was removed for tests, and after passing the tests, the traditional Chinese medicine composition was obtained.

Example 17 The Preparation of the Traditional Chinese Medicine Composition

Extraction: 0.5 g honeysuckle, 1 g tangerine peel and 5 g stir-baked malt were weighed in proportion according to the formulation, and these materials were put into an extraction tank, then after the addition of 10 times of water the extraction was performed at 92° C. for 3 hours and repeated twice to obtain an extract, which was concentrated into a concentrate with a soluble solids content of 15-25%.

Formulation: the ingredients were weighed in proportion according to the formulation, and to the formulation tank were added: 31.5 g water, 10 g honey, 15 g hawthorn juice, 30 g sugar cane juice and the concentrate described above. After the intermediates were stirred continuously for 10-15 min, the stirring was stopped and a sample was removed for tests, and after passing the tests, the traditional Chinese medicine composition was obtained.

Example 18 The Preparation of the Traditional Chinese Medicine Composition

Extraction: 1 g honeysuckle, 5 g tangerine peel and 10 g stir-baked malt were weighed in proportion according to the formulation, and these materials were put into an extraction tank, then after the addition of 12 times of water the extraction was performed at 95° C. for 2 hours and repeated twice to obtain an extract, which was concentrated into a concentrate with a soluble solids content of 15-25%.

Formulation: the ingredients were weighed in proportion according to the formulation, and to the formulation tank were added: 24.0 g water, 15 g honey, 20 g hawthorn juice, 10 g sugar cane juice, and the concentrate described above. After the intermediates were stirred continuously for 10-15 min, the stirring was stopped and a sample was removed for tests, and after passing the tests, the traditional Chinese medicine composition was obtained.

Example 19 The Preparation of the Traditional Chinese Medicine Composition

Extraction: 5 g honeysuckle, 10 g tangerine peel and 0.5 g stir-baked malt were weighed in proportion according to the formulation, and these materials were put into an extraction tank, then after the addition of 14 times of water the extraction was performed at 100° C. for 3 hours and repeated three times to obtain an extract, which was concentrated into a concentrate with a soluble solids content of 15-25%.

Formulation: the ingredients were weighed in proportion according to the formulation, and to the formulation tank were added: 16.5 g water, 20 g honey, 5 g hawthorn juice, 20 g sugar cane juice and the concentrate described above. After the intermediates were stirred continuously for 10-15 min, the stirring was stopped and a sample was removed for tests, and after passing the tests, the traditional Chinese medicine composition was obtained.

Example 20 The Preparation of the Traditional Chinese Medicine Composition

Extraction: 10 g honeysuckle, 0.5 g tangerine peel and 1 g stir-baked malt were weighed in proportion according to the formulation, and these materials were put into an extraction tank, then after the addition of 15 times of water the extraction was performed at 90° C. for 2 hours and repeated three times to obtain an extract, which was concentrated into a concentrate with a soluble solids content of 15-25%.

Formulation: the ingredients were weighed in proportion according to the formulation, and to the formulation tank were added: 18.5 g water, 5 g honey, 10 g hawthorn juice, 25 g sugar cane juice, and the concentrate described above. After the intermediates were stirred continuously for 10-15 min, the stirring was stopped and a sample was removed for tests, and after passing the tests, the traditional Chinese medicine composition was obtained.

Example 21 The Preparation of the Traditional Chinese Medicine Composition

Extraction: 0.5 g honeysuckle, 1 g tangerine peel and 5 g stir-baked malt were weighed in proportion according to the formulation, and these materials were put into an extraction tank, then after the addition of 10 times of water the extraction was performed at 92° C. for 3 hours and repeated twice to obtain an extract, which was concentrated into a concentrate with a soluble solids content of 15-25%.

Formulation: the ingredients were weighed in proportion according to the formulation, and to the formulation tank were added: 31.5 g water, 10 g honey, 15 g hawthorn juice, 30 g sugar cane juice, 2 g grape juice and the concentrate described above. After the intermediates were stirred continuously for 10-15 min, the stirring was stopped and a sample was removed for tests, and after passing the tests, the traditional Chinese medicine composition was obtained.

Example 22 The Preparation of the Traditional Chinese Medicine Composition

Extraction: 1 g honeysuckle, 5 g tangerine peel and 10 g stir-baked malt were weighed in proportion according to the formulation, and these materials were put into an extraction tank, then after the addition of 12 times of water the extraction was performed at 95° C. for 2 hours and repeated twice to obtain an extract, which was concentrated into a concentrate with a soluble solids content of 15-25%.

Formulation: the ingredients were weighed in proportion according to the formulation, and to the formulation tank were added: 24.0 g water, 15 g honey, 20 g hawthorn juice, 10 g sugar cane juice, 5 g grape juice and the concentrate described above. After the intermediates were stirred continuously for 10-15 min, the stirring was stopped and a sample was removed for tests, and after passing the tests, the traditional Chinese medicine composition was obtained.

Example 23 The Preparation of the Traditional Chinese Medicine Composition

Extraction: 5 g honeysuckle, 10 g tangerine peel and 0.5 g stir-baked malt were weighed in proportion according to the formulation, and these materials were put into an extraction tank, then after the addition of 14 times of water the extraction was performed at 100° C. for 3 hours and repeated three times to obtain an extract, which was concentrated into a concentrate with a soluble solids content of 15-25%.

Formulation: the ingredients were weighed in proportion according to the formulation, and to the formulation tank were added: 16.5 g water, 20 g honey, 5 g hawthorn juice, 20 g sugar cane juice, 8 g grape juice and the concentrate described above. After the intermediates were stirred continuously for 10-15 min, the stirring was stopped and a sample was removed for tests, and after passing the tests, the traditional Chinese medicine composition was obtained.

Example 24 The Preparation of the Traditional Chinese Medicine Composition

Extraction: 10 g honeysuckle, 0.5 g tangerine peel and 1 g stir-baked malt were weighed in proportion according to the formulation, and these materials were put into an extraction tank, then after the addition of 15 times of water the extraction was performed at 90° C. for 2 hours and repeated three times to obtain an extract, which was concentrated into a concentrate with a soluble solids content of 15-25%.

Formulation: the ingredients were weighed in proportion according to the formulation, and to the formulation tank were added: 18.5 g water, 5 g honey, 10 g hawthorn juice, 25 g sugar cane juice, 10 g grape juice and the concentrate described above. After the intermediates were stirred continuously for 10-15 min, the stirring was stopped and a sample was removed for tests, and after passing the tests, the traditional Chinese medicine composition was obtained.

Example 25 The Preparation of the Traditional Chinese Medicine Composition

Extraction: 0.5 g honeysuckle, 1 g tangerine peel and 5 g stir-baked malt were weighed in proportion according to the formulation, and these materials were put into an extraction tank, then after the addition of 10 times of water the extraction was performed at 92° C. for 3 hours and repeated twice to obtain an extract, which was concentrated into a concentrate with a soluble solids content of 15-25%.

Formulation: the ingredients were weighed in proportion according to the formulation, and to the formulation tank were added: 31.5 g water, 5 g crystal sugar, 10 g honey, 15 g hawthorn juice, 2 g grape juice and the concentrate described above. After the intermediates were stirred continuously for 10-15 min, the stirring was stopped and a sample was removed for tests, and after passing the tests, the traditional Chinese medicine composition was obtained.

Example 26 The Preparation of the Traditional Chinese Medicine Composition

Extraction: 1 g honeysuckle, 5 g tangerine peel and 10 g stir-baked malt were weighed in proportion according to the formulation, and these materials were put into an extraction tank, then after the addition of 12 times of water the extraction was performed at 95° C. for 2 hours and repeated twice to obtain an extract, which was concentrated into a concentrate with a soluble solids content of 15-25%.

Formulation: the ingredients were weighed in proportion according to the formulation, and to the formulation tank were added: 24.0 g water, 10 g crystal sugar, 15 g honey, 20 g hawthorn juice, 5 g grape juice and the concentrate described above. After the intermediates were stirred continuously for 10-15 min, the stirring was stopped and a sample was removed for tests, and after passing the tests, the traditional Chinese medicine composition was obtained.

Example 27 The Preparation of the Traditional Chinese Medicine Composition

Extraction: 5 g honeysuckle, 10 g tangerine peel and 0.5 g stir-baked malt were weighed in proportion according to the formulation, and these materials were put into an extraction tank, then after the addition of 14 times of water the extraction was performed at 100° C. for 3 hours and repeated three times to obtain an extract, which was concentrated into a concentrate with a soluble solids content of 15-25%.

Formulation: the ingredients were weighed in proportion according to the formulation, and to the formulation tank were added: 16.5 g water, 15 g crystal sugar, 20 g honey, 5 g hawthorn juice, 8 g grape juice and the concentrate described above. After the intermediates were stirred continuously for 10-15 min, the stirring was stopped and a sample was removed for tests, and after passing the tests, the traditional Chinese medicine composition was obtained.

Example 28 The Preparation of the Traditional Chinese Medicine Composition

Extraction: 10 g honeysuckle, 0.5 g tangerine peel and 1 g stir-baked malt were weighed in proportion according to the formulation, and these materials were put into an extraction tank, then after the addition of 15 times of water the extraction was performed at 90° C. for 2 hours and repeated three times to obtain an extract, which was concentrated into a concentrate with a soluble solids content of 15-25%.

Formulation: the ingredients were weighed in proportion according to the formulation, and to the formulation tank were added: 18.5 g water, 20 g crystal sugar, 5 g honey, 10 g hawthorn juice, 10 g grape juice and the concentrate described above. After the intermediates were stirred continuously for 10-15 min, the stirring was stopped and a sample was removed for tests, and after passing the tests, the traditional Chinese medicine composition was obtained.

Example 29 The Preparation of the Traditional Chinese Medicine Composition

Extraction: 0.5 g honeysuckle, 1 g tangerine peel and 5 g stir-baked malt were weighed in proportion according to the formulation, and these materials were put into an extraction tank, then after the addition of 10 times of water the extraction was performed at 92° C. for 3 hours and repeated twice to obtain an extract, which was concentrated into a concentrate with a soluble solids content of 15-25%.

Formulation: the ingredients were weighed in proportion according to the formulation, and to the formulation tank were added: 31.5 g water, 10 g honey, 15 g hawthorn juice, 2 g grape juice and the concentrate described above. After the intermediates were stirred continuously for 10-15 min, the stirring was stopped and a sample was removed for tests, and after passing the tests, the traditional Chinese medicine composition was obtained.

Example 30 The Preparation of the Traditional Chinese Medicine Composition

Extraction: 1 g honeysuckle, 5 g tangerine peel and 10 g stir-baked malt were weighed in proportion according to the formulation, and these materials were put into an extraction tank, then after the addition of 12 times of water the extraction was performed at 95° C. for 2 hours and repeated twice to obtain an extract, which was concentrated into a concentrate with a soluble solids content of 15-25%.

Formulation: the ingredients were weighed in proportion according to the formulation, and to the formulation tank were added: 24.0 g water, 15 g honey, 20 g hawthorn juice, 5 g grape juice and the concentrate described above. After the intermediates were stirred continuously for 10-15 min, the stirring was stopped and a sample was removed for tests, and after passing the tests, the traditional Chinese medicine composition was obtained.

Example 31 The Preparation of the Traditional Chinese Medicine Composition

Extraction: 5 g honeysuckle, 10 g tangerine peel and 0.5 g stir-baked malt were weighed in proportion according to the formulation, and these materials were put into an extraction tank, then after the addition of 14 times of water the extraction was performed at 100° C. for 3 hours and repeated three times to obtain an extract, which was concentrated into a concentrate with a soluble solids content of 15-25%.

Formulation: the ingredients were weighed in proportion according to the formulation, and to the formulation tank were added: 16.5 g water, 20 g honey, 5 g hawthorn juice, 8 g grape juice and the concentrate described above. After the intermediates were stirred continuously for 10-15 min, the stirring was stopped and a sample was removed for tests, and after passing the tests, the traditional Chinese medicine composition was obtained.

Example 32 The Preparation of the Traditional Chinese Medicine Composition

Extraction: 10 g honeysuckle, 0.5 g tangerine peel and 1 g stir-baked malt were weighed in proportion according to the formulation, and these materials were put into an extraction tank, then after the addition of 15 times of water the extraction was performed at 90° C. for 2 hours and repeated three times to obtain an extract, which was concentrated into a concentrate with a soluble solids content of 15-25%.

Formulation: the ingredients were weighed in proportion according to the formulation, and to the formulation tank were added: 18.5 g water, 5 g honey, 10 g hawthorn juice, 10 g grape juice and the concentrate described above. After the intermediates were stirred continuously for 10-15 min, the stirring was stopped and a sample was removed for tests, and after passing the tests, the traditional Chinese medicine composition was obtained.

Example 33 Tests of Effects

1 Experimental Samples and Methods
1.1 Experimental Samples

The traditional Chinese medicine compositions of Examples 1 to 8 of the present application were taken as experimental samples, the composition of Example 3 in Publication No. CN 102511880A as Control A, the composition of Example 1 disclosed in Publication No. CN 103417876 A as Control B, and pure water as Control C.
1.2 Experimental Objects Adult rats were taken as experimental objects, and divided into 11 groups, that is, Example 1 to 8 groups, Control A group, Control B group and Control C group to conduct the experiments, with an amount of 20 rats in each group.

The rats were filled and fed using Example 1 to 8 groups, Control A, Control B and Control C 5 days a week for two weeks.
1.3 Experimental Methods The gastric emptying rate, intestinal motility, gastric digestive enzymes (pepsin) and pancreatic enzymes (trypsin, chymotrypsin, amylase and lipase) activity of rats were detected, and the effects of the tested samples were evaluated by comparing the experimental sample groups, A group and B group with C group respectively.
2. Experimental Results

TABLE 1

The gastric emptying rates of the rats in different groups

| Group | 2 Weeks |
| --- | --- |
| Example 1 | 28% |
| Example 2 | 30% |
| Example 3 | 25% |
| Example 4 | 24% |
| Example 5 | 27% |
| Example 6 | 26% |
| Example 7 | 29% |
| Example 8 | 25% |
| Control A | 8% |
| Control B | 17% |
| Control C | no significant effects |

TABLE 2

The intestinal motility of the rats in different groups

| Group | 2 Weeks |
| --- | --- |
| Example 1 | 25% |
| Example 2 | 27% |
| Example 3 | 26% |
| Example 4 | 24% |
| Example 5 | 26% |
| Example 6 | 28% |
| Example 7 | 24% |
| Example 8 | 27% |
| Control A | 5% |
| Control B | 15% |
| Control C | no significant effects |

TABLE 3

The pepsin activity of the rats in different groups

| Group | 2 Weeks |
| --- | --- |
| Example 1 | 30% |
| Example 2 | 32% |
| Example 3 | 27% |
| Example 4 | 26% |
| Example 5 | 31% |
| Example 6 | 32% |
| Example 7 | 28% |
| Example 8 | 29% |
| Control A | 10% |
| Control B | 16% |
| Control C | no significant effects |

TABLE 4

The pancreatic enzyme activity of the rats in different groups

| Group | Trypsin | Chymotrypsin | Amylase | Lipase |
| --- | --- | --- | --- | --- |
| Example 1 | 12% | 15% | 23% | 44% |
| Example 2 | 14% | 16% | 27% | 43% |
| Example 3 | 13% | 14% | 22% | 40% |
| Example 4 | 10% | 15% | 24% | 41% |
| Example 5 | 13% | 14% | 26% | 43% |
| Example 6 | 14% | 15% | 25% | 42% |
| Example 7 | 12% | 16% | 25% | 44% |
| Example 8 | 12% | 15% | 27% | 41% |
| Control A | no significant effects | no significant effects | 4% | 5% |
| Control B | 5% | 10% | 10% | 20% |
| Control C | no significant effects | no significant effects | no significant effects | no significant effects |

As seen from Table 1, the compositions of Examples 1 to 8 of the present invention may significantly improve the gastric emptying rates (24% to 30%) of rats, which are substantially higher than those of Control A (8%) and Control B (17%).

As seen from Table 2, the compositions of Examples 1 to 8 of the present invention may significantly improve the intestinal motility (24% to 28%) of rats, which are substantially higher than those of Control A (5%) and Control B (15%).

As seen from Table 3, the compositions of Examples 1 to 8 of the present invention may significantly improve the pepsin activity (26% to 32%) of rats, which are substantially higher than those of Control A (10%) and Control B (16%).

As seen from Table 4, the compositions of Examples 1 to 8 of the present invention may significantly improve the trypsin (10% to 14%), chymotrypsin (14% to 16%), amylase (22% to 27%) and lipase (40% to 44%) activity of rats, which are substantially higher than those of Control A (8%) and Control B (17%).

A comprehensive analysis of the results above shows that the obtained compositions of the present invention have significant promotions on the gastric emptying rate, intestinal motility, gastric digestive enzyme (pepsin) activity and pancreatic enzyme (trypsin, chymotrypsin, amylase and lipase) activity of rats, which are superior to those of Control A and Control B, exhibiting that the traditional Chinese medicine compositions of the present invention have significant effects of clearing heat, lowering fire and moistening the intestine.

Example 34 The Preparation of the Juice Beverage

Homogenization: the traditional Chinese medicine composition obtained in Example 1 was taken and pre-heated to 60° C. before entering the homogenizer having a pressure of 30 Mpa.

Sterilization: The intermediates were sterilized using UHT sterilizer at a sterilizing temperature of 120° C. for a sterilizing time of 30 s.

Bottling: the bottling temperature is 65-75° C., and the bottling concentration is generally 45-55%.

Cooling: the concentrate after bottling was cooled by water spraying at normal temperature for 30 min, with a temperature after cooling <40° C.

Light examination and packaging were performed to obtain the juice beverage.

Example 35 The Preparation of the Juice Beverage

Homogenization: the traditional Chinese medicine composition obtained in Example 2 was taken and pre-heated to 65° C. before entering the homogenizer having a pressure of 20 Mpa.

Sterilization: The intermediates were sterilized using UHT sterilizer at a sterilizing temperature of 130° C. for a sterilizing time of 10 s.

Bottling: the bottling temperature is 65-75° C., and the bottling concentration is generally 45-55%.

Cooling: the concentrate after bottling was cooled by water spraying at normal temperature for 30 min, with a temperature after cooling <40° C.

Light examination and packaging were performed to obtain the juice beverage.

Example 36 The Preparation of the Juice Beverage

Homogenization: the traditional Chinese medicine composition obtained in Example 3 was taken and pre-heated to 70° C. before entering the homogenizer having a pressure of 15 Mpa.

Sterilization: The intermediates were sterilized using UHT sterilizer at a sterilizing temperature of 135° C. for a sterilizing time of 5 s.

Bottling: the bottling temperature is 65-75° C., and the bottling concentration is generally 45-55%.

Cooling: the concentrate after bottling was cooled by water spraying at normal temperature for 30 min, with a temperature after cooling <40° C.

Light examination and packaging were performed to obtain the juice beverage.

The above description gives only the preferred embodiments of the present invention, and it should be noted that for those of ordinary skill in the art, a number of improvements and modifications can be made without departing from the principle of the invention, which are also regarded as falling into the scope claimed in the present invention.

The invention claimed is:

1. A composition for increasing the gastric emptying rate and improving the intestinal motility of a human in need thereof consisting essentially of 0.5-10 parts of honeysuckle extract, 0.5-10 parts of tangerine peel, 0.5-10 parts of stir-baked malt, 5-20 parts of crystal sugar, 5-20 parts honey, 5-20 parts hawthorn juice, 10-30 parts sugar cane juice, and 2-10 parts grape juice.

2. A method for increasing the gastric emptying rate and improving the intestinal motility in a subject in need thereof consisting essentially of administering to the subject a therapeutically effective amount of the traditional Chinese medicine composition according to claim 1.

* * * * *

UNITED STATES PATENT AND TRADEMARK OFFICE
CERTIFICATE OF CORRECTION

PATENT NO. : 9,950,024 B2
APPLICATION NO. : 15/164844
DATED : April 24, 2018
INVENTOR(S) : Shiyu Zou, Jiangping Li and Chung Wah Ma Page 1 of 1

It is certified that error appears in the above-identified patent and that said Letters Patent is hereby corrected as shown below:

In the Specification

At Column 19, Line 29, the expression "a temperature after cooling < 40 °C" should be deleted and replaced with "a temperature after cooling ≤ 40 °C".

At Column 20, Line 3, the expression "a temperature after cooling < 40 °C" should be deleted and replaced with "a temperature after cooling ≤ 40 °C".

At Column 20, Line 20, the expression "a temperature after cooling < 40 °C" should be deleted and replaced with "a temperature after cooling ≤ 40 °C".

Signed and Sealed this
Ninth Day of October, 2018

Andrei Iancu
*Director of the United States Patent and Trademark Office*